(12) United States Patent
Gwak et al.

(10) Patent No.: US 9,376,370 B2
(45) Date of Patent: *Jun. 28, 2016

(54) METHOD FOR PURIFYING 1,4-DIAMINOBUTANE, 1,4-DIAMINOBUTANE PURIFIED BY SAID METHOD, AND POLYAMIDE PREPARED THEREFROM

(71) Applicant: CJ CHEILJEDANG CORP., Seoul (KR)

(72) Inventors: Won Sik Gwak, Gimpo-si (KR); Yong Bum Seo, Gimpo-si (KR); Chong Ho Lee, Seoul (KR); In Sung Lee, Seoul (KR); Hideki Murata, Seoul (KR)

(73) Assignee: CJ CHEILJEDANG CORP. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/437,172

(22) PCT Filed: Oct. 22, 2013

(86) PCT No.: PCT/KR2013/009399
§ 371 (c)(1),
(2) Date: Apr. 20, 2015

(87) PCT Pub. No.: WO2014/065553
PCT Pub. Date: May 1, 2014

(65) Prior Publication Data
US 2015/0284315 A1    Oct. 8, 2015

(30) Foreign Application Priority Data

Oct. 22, 2012   (KR) .................. 10-2012-0117501

(51) Int. Cl.
*C07C 209/84* (2006.01)
*C07C 211/09* (2006.01)
*C08G 69/26* (2006.01)
*C12P 13/00* (2006.01)

(52) U.S. Cl.
CPC ............. *C07C 209/84* (2013.01); *C07C 211/09* (2013.01); *C08G 69/26* (2013.01); *C12P 13/001* (2013.01)

(58) Field of Classification Search
CPC .... C07C 209/84; C07C 211/09; C08G 69/04; C08G 69/26; C12P 13/001
See application file for complete search history.

(56) References Cited

U.S. PATENT DOCUMENTS

| 7,977,514 | B2 * | 7/2011 | Peters ................... | C07C 209/86 |
| | | | | 564/497 |
| 8,334,411 | B2 * | 12/2012 | Ito ........................ | B01D 61/027 |
| | | | | 564/138 |
| 8,927,774 | B2 * | 1/2015 | Gwak ................... | C07C 209/84 |
| | | | | 435/128 |
| 2010/0203599 | A1 | 8/2010 | Lee et al. | |
| 2010/0274057 | A1 | 10/2010 | Peters et al. | |
| 2010/0292429 | A1 * | 11/2010 | Volkert ................ | C07C 209/84 |
| | | | | 528/44 |
| 2011/0004018 | A1 | 1/2011 | Ito et al. | |

FOREIGN PATENT DOCUMENTS

| KR | 1020080108082 | 12/2008 |
| KR | 1020090107920 | 8/2010 |
| KR | 1020100117084 | 11/2010 |
| KR | 1020100133366 | 12/2010 |

OTHER PUBLICATIONS

International Search Report—PCT/KR2013/009399 dated Jan. 23, 2014.
Written Opinion—PCT/KR2013/009399 dated Jan. 23, 2014.

* cited by examiner

*Primary Examiner* — Shailendra Kumar
(74) *Attorney, Agent, or Firm* — Cantor Colburn LLP

(57) ABSTRACT

A purification method of 1,4-diaminobutane, 1,4-diaminobutane purified using the purification method, and a polyamide prepared using the purified 1,4-diaminobutane are provided. The purification method of 1,4-diaminobutane includes: concentrating a fermentation solution including at least one of 1,4-diaminobutane and a salt thereof to obtain a concentrate; adding a base to the concentrate of the fermentation solution to prepare an basic composition having a pH 12 or higher; and recovering 1,4-diaminobutane from the basic composition.

20 Claims, 1 Drawing Sheet

METHOD FOR PURIFYING 1,4-DIAMINOBUTANE, 1,4-DIAMINOBUTANE PURIFIED BY SAID METHOD, AND POLYAMIDE PREPARED THEREFROM

This application is a 371 of PCT/KR2013/009399, filed on Oct. 22, 2013.

TECHNICAL FIELD

The present disclosure relates to a method of purifying 1,4-diaminobutane, 1,4-diaminobutane purified using the method, and a polyamide prepared using the 1,4-diaminobutane.

BACKGROUND ART 1,4-diaminobutane (also called as putrescine) may be prepared via hydrogenation and distillation of succinonitrile prepared from hydrogen cyanide and acrylonitrile. 1,4-diaminobutane may also be prepared via distillation after adding an alkali metal phthalimide catalyst and hydrazine to 1,4-dibromobutane or 1,4-dichlorobutane. These chemical synthesis methods of 1,4-diaminobutane use a toxic compound such as hydrogen cyanide or require an expensive reaction catalyst.

Recently, there has been research into methods of producing 1,4-diaminobutane through fermentation without using any toxic compound and/or expensive catalyst. However, 1,4-diaminobutane obtained through fermentation is conventionally provided at a low concentration in a fermentation solution, combined with a salt.

Therefore, there is a need for an effective method of purifying 1,4-diaminobutane from the fermentation solution.

DETAILED DESCRIPTION OF THE DISCLOSURE

Technical Problem

The present disclosure provides a novel method of purifying 1,4-diaminobutane.

The present disclosure also provides 1,4-diaminobutane purified using the novel purification method.

The present disclosure also provides a polyamide prepared using the purified 1,4-diaminobutane.

Technical Solution

According to an aspect of the present disclosure, a method of purifying 1,4-diaminobutane includes: concentrating a fermentation solution including at least one of 1,4-diaminobutane and a salt thereof to obtain a concentrate; adding a base to the concentrate of the fermentation solution to prepare an basic composition having a pH 12 or higher; and recovering 1,4-diaminobutane from the basic composition.

According to another aspect of the present disclosure, there is provided a 1,4-diaminobutane purified by the above-described method.

According to another aspect of the present disclosure, there is provided a polyamide prepared using the 1,4-diaminobutane.

Advantageous Effects

As described above, high-purity 1,4-diaminobutane may be obtained with a high yield by adding a base to a 1,4-diaminobutane-including fermentation solution.

BEST MODE

Figure 1:
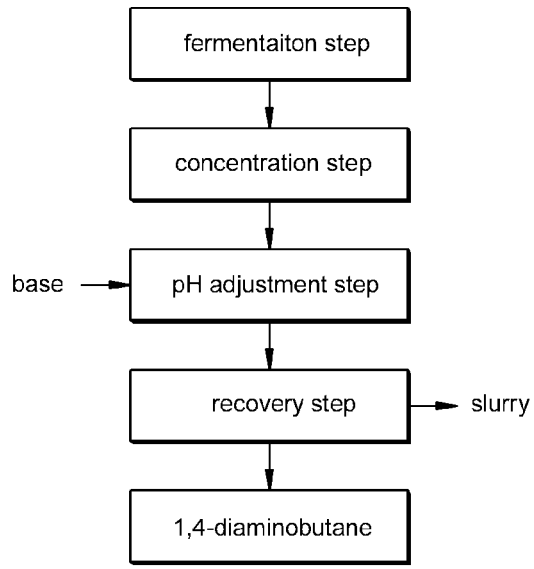
FIG. 1 is a flowchart of a method of purifying 1,4-diaminobutane in Example 1.
Figure 2:
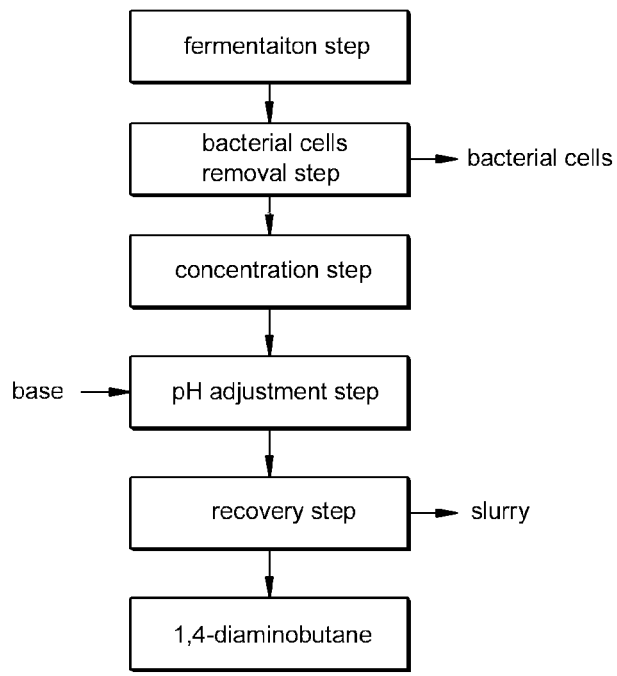
FIG. 2 is a flowchart of a method of purifying 1,4-diaminobutane in Example 2.

Hereinafter, embodiments of a method of purifying 1,4-diaminobutane, 1,4-diaminobutane purified using the method, and polyamide prepared using the 1,4-diaminobutane will be described in greater detail.

According to an aspect of the present disclosure, a method of purifying 1,4-diaminobutane includes: concentrating a fermentation solution containing at least one of 1,4-diaminobutane and a salt thereof to obtain a concentrate; adding a base to the concentrate of the fermentation solution to prepare an basic composition having a pH 12 or higher; and recovering 1,4-diaminobutane from the basic composition.

In some embodiments of the purification method, a high-purity 1,4-diaminobutane may be easily obtained with a high yield by concentrating a neutral fermentation solution containing a salt of 1,4-diaminobutane, adding a base thereto to isolate 1,4-diaminobutane from the salt of 1,4-diaminobutane, and then selectively recovering 1,4-diaminobutane.

The fermentation solution may be neutral. In the concentrating of the fermentation solution (first concentration step), at least part of a solvent in the fermentation solution may be removed. The concentration of 1,4-diaminobutane in the fermentation solution may be increased as at least part of the solvent is removed. The solvent may be water. For example, the amount of the solvent removed during the concentrating of a fermentation solution may be about 50% or more, and in some embodiments, about 60% or more, and in some other embodiments, about 70% or more, and in still other embodiments, about 80% or more of the amount of the solvent in the fermentation solution before the concentrating.

The concentrating of the fermentation solution may be performed in a low temperature and reduced pressure environment to prevent destruction of bacterial cells that are usually contained in the fermentation solution.

In some embodiments of the purification method, the concentrating of the fermentation solution may be performed at a vapor temperature of about 100° C. or less, i.e., under the condition in which the temperature of vapor evaporated from the fermentation solution is about 100° C. or less. For example, the concentrating of the fermentation solution may be performed at a vapor temperature of about 10° C. to about 100° C., and in some embodiments, about 30° C. to about 80° C., and in some other embodiments, about 45° C. to about 67° C. The solvent of the fermentation solution may be more easily removed in these conditions.

In some embodiments of the purification method, the concentrating of the fermentation solution may be performed at a reduced pressure of about 760 mmHg or less, i.e., under the condition in which a pressure of vapor in equilibrium with the fermentation solution is about 760 mmHg or less. For example, the concentrating of the fermentation solution may be performed at a pressure of about 10 mmHg to about 760 mmHg, and in some embodiments, about 40 mmHg to about 500 mmHg, and in some other embodiments, about 70 mmHg to about 200 mmHg. The solvent of the fermentation solution may be more easily removed in these conditions.

In some embodiments, the purification method may further include removing bacterial cells from the fermentation solution before the concentrating of the fermentation solution.

The removing of bacterial cells from the fermentation solution before the concentrating of the fermentation solution may increase the purify of 1,4-diaminobutane obtained through the purification. The removed bacterial cells may be used as a byproduct, for example, as animal feed after being dried.

The removing of bacterial cells from the fermentation solution may be performed using any method available in the art, not specifically limited, for example, using centrifugation, filter pressing, diatomite filtering, rotary vacuum filtering, membrane filtering, or coagulating/floating.

The amount of the solvent in the concentrate (i.e., concentrated product) resulting from the concentrating of the fermentation solution may be in a range of about 10 wt % to about 50 wt % based on a total weight of the concentrate. For example, the amount of the solvent in the concentrate may be in a range of about 15 wt % to about 45 wt %, and in some embodiments, about 20 wt % to about 40 wt %, based on the total weight of the concentrated product. When the amount of the solvent in the concentrate is too small, an excess of salt may be precipitated in the preparing of the basic composition. When the amount of the solvent in the concentrate is too large, it may take a long time to remove 1,4-diaminobutane from the basic composition, thus may result in a carbonate salt of 1,4-diaminobutane. The solvent may be water.

In some embodiments of the purification method, the fermentation solution may be prepared through fermentation. The fermentation solution may be prepared by culturing a microorganism, for example, a mutated microorganism. The culturing of a microorganism may be performed by, for example, batch culturing, continuous culturing, or fed-batch culturing, but not limited thereto, by any method available in the art.

In some embodiments of the purification method, the base used to prepare the basic composition may be at least one selected from the group consisting of sodium hydroxide, calcium hydroxide, magnesium hydroxide, potassium hydroxide, barium hydroxide, and ammonium hydroxide, but is not limited thereto. The base may be any base available in the art to adjust the pH of a composition to a basic pH.

In some embodiments of the purification method, the basic composition may have a pH of about 12 or higher, and in some embodiments, about 12.0 to about 14.0. When the basic composition has a pH of less than 12.0, 1,4-diaminobutane may be present, partially combined with a salt, and thus it may be difficult to separate 1,4-diaminobutane by distillation, consequently resulting in a reduced recovery of 1,4-diaminobutane.

In some embodiments of the purification method, the recovering of 1,4-diaminobutane may be performed before a carbonate salt of 1,4-diaminobutane is formed in the basic composition. A carbonate salt of 1,4-diaminobutane may be formed as 1,4-diaminobutane in the basic solution binds with oxygen in the air with time, which may reduce the amount of 1,4-diaminobutane recovered by distillation. For this reason, the recovering of 1,4-diaminobutane may be performed immediately after or at the same time as the preparation of the basic solution.

In some embodiments of the purification method, the recovering of 1,4-diaminobutane from the basic composition may include separating a 1,4-diaminobutane-including composition from the basic composition by distillation (second concentration step) and separating 1,4-diaminobutane from the 1,4-diaminobutane-including composition by fractional distillation.

For example, the 1,4-diaminobutane-including composition may be stored after separated from the basic composition, and the recovering of 1,4-diaminobutane from the 1,4-diaminobutane-including composition may be performed upon need. The 1,4-diaminobutane-including composition may be a composition containing 1,4-diaminobutane more than in the basic composition and less than in a final purified product.

In some embodiments of the purification method, the 1,4-diaminobutane-including composition may be in a gaseous state, a liquid state, or a mixed state thereof. The state of 1,4-diaminobutane-including composition may be varied depending on required purification conditions.

In some embodiments, a 1,4-diaminobutane-including composition in a gaseous state and/or in a condensate state may be separated from the basic composition by distillation. The separating of the 1,4-diaminobutane-including composition by distillation may be performed using a double jacketed reactor.

In some embodiments of the purification method, the separating of the 1,4-diaminobutane-including composition may be performed at a vapor temperature of about 30° C. to about 158° C. and a pressure of about 10 mmHg to about 760 mmHg, and in some embodiments, at a vapor temperature of about 40° C. to about 120° C. and a pressure of about 70 mmHg to about 200 mmHg. The 1,4-diaminobutane-including composition may be separated with a high yield under these conditions. The 1,4-diaminobutane-including composition separated within these temperature and pressure ranges may be in a liquid state via condensation.

The separated 1,4-diaminobutane-including composition may be stored, for example, in a reservoir disposed between a top of the reactor and a distillation tower, but not limited thereto. The separated 1,4-diaminobutane-including composition may be stored in any manner available in the art.

In some embodiments of the purification method, the separating of the 1,4-diaminobutane-including composition from the basic composition by distillation and the recovering of 1,4-diaminobutane from the 1,4-diaminobutane-including composition by fractional distillation may be continuously performed. In other words, the 1,4-diaminobutane-including composition may be separated from the basic solution by distillation and at the same time the composition may be further separated into 1,4-diaminobutane and other components by fractional distillation to selectively recover 1,4-diaminobutane. The 1,4-diaminobutane recovered by fractional distillation may be a final product.

In some embodiments of the purification method, the recovering of 1,4-diaminobutane by fractional distillation may be performed using a distillation tower. For example, the 1,4-diaminobutane-including composition, vaporized from the reactor containing the basic composition, may continuously flow into the distillation tower to selectively recover 1,4-diaminobutane therefrom. For example, the 1,4-diaminobutane-including composition may be introduced into a middle region of the distillation tower. The region to which the 1,4-diaminobutane-including composition is supplied may be varied depending on reaction conditions and distillation tower conditions.

In some embodiments of the purification method, the distillation tower may be operated at a vapor temperature of about 30° C. to about 158° C. and a pressure of about 10 mmHg to about 760 mmHg, and in some embodiments, at a vapor temperature of about 80° C. to about 120° C. and a pressure of about 70 mmHg to about 200 mmHg. 1,4-diaminobutane may be obtained with a high yield within these temperature and pressure ranges.

In some embodiments of the purification method, 1,4-diaminobutane may be recovered in a low region of the distillation tower, and for example, water and ammonia may be recovered in an upper region of the distillation tower.

In some embodiments of the purification method, after the separating of the 1,4-diaminobutane-including composition from the basic composition, a byproduct may be recovered from the a residual slurry. For example, a byproduct may be recovered from the residual slurry through further purification. When the residual slurry includes bacterial cells, a byproduct may be recovered after completely dissolving the residual slurry with water and removing the bacterial cells therefrom.

The byproduct may be, for example, at least one selected from the group consisting of sodium sulfate, potassium sulfate, magnesium sulfate, lithium sulfate, barium sulfate, and ammonium sulfate.

For example, 1,4-diaminobutane may be purified as follows.

Fermentation Step

First, a fermentation solution including 1,4-diaminobutane and a salt thereof may be prepared by culturing a microorganism, i.e., bacterial cells.

The microorganism used in this fermentation step may be a mutated *Corynebacterium* microorganism or a mutated *Escherichia coli*. The culturing of a microorganism may be performed using a known method such as batch culturing, continuous culturing, or fed-batch culturing. As a culture condition, the pH of the fermentation solution may be adjusted with an basic composition to pH 7. After oxygen or an oxygen-containing gas mixture was added to the fermentation solution, the fermentation solution may be cultured at a temperature of about 20° C. to about 45° C., and in some embodiments, about 25° C. to about 40° C., for about 10 hours to about 160 hours. A culture medium used herein may be, for example, a mixture of a XQ37/pKKSpeC strain, glucose, and ammonium sulfate $((NH_2)_2SO_4)$. The XQ37/pKKSpeC strain may be prepared in the same manner as disclosed in Korean Patent Application No. 2009-0107920.

Bacterial Cell Removal Step

Next, bacterial cells may be removed from the fermentation solution. The removing of bacterial cells may be omitted.

The removing of bacterial cells from the fermentation solution may be performed using any method, for example, not limited to, centrifugation, filter pressing, diatomite filtering, rotary vacuum filtering, membrane filtering, or coagulating/floating. For example, the removing of bacterial cells may be performed using a membrane filter. The neutral fermentation solution may be separated through a membrane filter into a filtrate and bacterial cell sludgy. Bacterial cells and other impurities unable to pass through micropores of the membrane filter may be removed, while only liquid passed though the micropores of the membrane filter may be obtained as a filtrate. The residual bacterial cell sludge or bacterial cell sludge solution not included in the filtrate because of an inability to pass through the micro-cores of the membrane filter may be separated and removed from the neutral fermentation solution. The membrane filter may be any filterable to remove bacterial cells from the neutral fermentation solution. The operating conditions of the membrane filter to separate and remove bacterial cells from the neutral fermentation solution may be easily set by one of ordinary skill in the art. For example, the neutral fermentation solution may be preheated at about 50° C. before the removing of bacterial cells. This is for increasing a bacterial cells removal efficiency. When the preheating of the neutral fermentation solution is performed at about 50° C., the filtrate may pass through the filter at a higher rate than at a temperature lower than 50° C., thus decreasing the filtration time, and consequently an increased productivity may also be expected. The filtration may be performed at a transmembrane pressure (TMP) of about 1.0 to 1.5 atm. The TMP is a pressure level exerted in a horizontal direction against fluid flowing in a vertical direction, i.e., a pressure exerted on the membrane by fluid) passing across the membrane filter tangentially. The pore size of the membrane filter may also be easily selected by one of ordinary skill in the art. For example, the pore size of the membrane filter may be in a range of about 0.01 μm to about 0.15 μm.

The membrane filter may have a time for gel layer formation on a surface of the membrane filter at its initial operation stage. This is for maintaining the permeate flux of the filtrate at a constant level for a long time by forming a thin layer of bacterial cells on the surface of the membrane filter. This operation may ensure a relatively constant permeate flux of the filtrate and may prevent frequent washing the membrane filter. Once the formation of the gel layer is complete, the filtrate may be obtained through the membrane filter.

First Concentration Step (Water Removal Step)

Next, the fermentation solution from which bacterial cells are removed or not may be concentrated by removing water therefrom.

The removing of water may be performed using a vacuum concentration method and/or an evaporation concentration method. Any concentrator, for example, not limited to, at least one selected from the group consisting of a centrifugation concentrator, an evaporation concentrator, a natural circulation evaporator, a low-temperature vacuum concentrator, a rotary vacuum concentrator, a vacuum evaporation concentrator, a thin film concentrator, and a planar concentrator may be used.

For example, the concentrating of the fermentation solution may be performed using low-temperature vacuum concentration. For example, the concentrating of the fermentation solution from which bacterial cells is removed or not may be performed at a vapor temperature of about 10° C. to about 100° C., for example, about 45° C. to about 70° C., and a pressure of about 10 mmHg to about 760 mmHg, for example, about 70 mmHg to about 200 mmHg. The resulting concentrate obtained by removing water from the fermentation solution may have a water content of about 15 wt % to about 45 wt %, and in some embodiments, about 20 wt % to about 40 wt %, and in some other embodiments, about 30 wt % to about 40 wt %, based on a total weight of the concentrated fermentation solution (i.e., the concentrate).

pH Adjustment Step

Next, a base may be added to the concentrated fermentation solution to adjust the pH of the concentrated fermented solution to a basic pH.

The pH of the concentrated fermentation solution may be adjusted by adding at least one base selected from the group consisting of sodium hydroxide, calcium hydroxide, magnesium hydroxide, potassium hydroxide, barium hydroxide, and ammonium hydroxide, for example, by adding sodium hydroxide. The basic fermentation solution may have a pH of about 12.0 or higher, and in some embodiments, about 12.0 to about 14.0. When the basic fermentation solution has a pH of less than 12.0, 1,4-diaminobutane may be present, partially combined with a salt, making it difficult to separate 1,4-diaminobutane from the basic fermentation solution. However, when the basic fermentation solution has a pH of 12 or higher, 1,4-diaminobutane may be present separate from a salt in the basic fermentation solution, and thus may be easily separated by distillation, consequently increasing a recovery of 1,4-diaminobutane.

Recovery Step

This recovery step may involve a second concentration step and a distillation step. These two steps practically may be continuously performed.

Second Concentration Step (Separation of 1,4-diaminobutane—including Vapor and/or Condensate)

Next, a vapor and/or condensate mainly including 1,4-diaminobutane may be separated from the basic concentrated fermentation solution.

In the second concentration step, the basic concentrated fermentation solution may be put into a concentrator and concentrated, for example, in a vacuum at a pressure of about 10 mm Hg to about 760 mmHg or at a pressure of about 70 mmHg to about 200 mmHg. The second concentration step may be performed, for example, at a temperature of about 30° C. to about 158° C. or at a temperature of about 40° C. to about 120° C.

The 1,4-diaminobutane—including vapor resulting from the second concentration step may be supplied via condensation or directly into a distillation tower for the next distillation step.

With evaporation of 1,4-diaminobutane from the concentrator during the second concentration step, the pH of a residual slurry in a lower region of the concentrator may be reduced. Accordingly, a base may be added to maintain the pH of the residual slurry at a pH of about 12.0 to about 14.0. In addition, distilled water may be added to the residual slurry to maintain a solid/liquid ratio at about 0.1 to about 2.0, and in some embodiments, about 0.5 to about 1.5.

The residual slurry resulting from the second concentration step may be further purified to obtain a byproduct. In the case where the fermentation solution is used without the separation of bacterial cells, distilled water may be added to completely dissolve the residual slurry and then to separate bacterial cells therefrom, followed by recovering a byproduct therefrom.

The recovered byproduct may be at least one selected from the group consisting of sodium sulfate, potassium sulfate, calcium sulfate, magnesium sulfate, potassium sulfate, lithium sulfate, barium sulfate, and ammonium sulfate, depending on the base used for the pH adjustment.

Distillation Step (High-purity 1,4-diaminobutane Recovery)

Next, high-purity 1,4-diaminobutane may be recovered from the vapor and/or condensate mainly including 1,4-diaminobutane.

This distillation step may be performed continuously with the second concentration step. For example, the 1,4-diaminobutane-including vapor from the second concentration step may be directly supplied into a middle-height region of a distillation tower.

The distillation step may be performed at a pressure of about 10 mmHg to about 760 mmHg or at a pressure of about 70 mmHg to about 200 mmHg. The distillation step may be performed, for example, at a temperature of about 30° C. to about 158° C. or at a temperature of about 40° C. to about 120° C.

When the distillation step is performed under these pressure and temperature conditions, water and ammonia may be obtained in an upper region of the distillation tower, while 1,4-diaminobutane may be recovered in a lower region of the distillation tower.

A 1,4-diaminobutane purified by a method according to the above-described embodiments may have a recovery of about 60 wt % or greater, and in some embodiments, about 65 wt % or greater, and in some other embodiments, about 75% or greater, and in still other embodiments, about 85% or greater, and in yet other embodiments, about 90.0 wt % or greater.

A 1,4-diaminobutane purified by a method according to the above-described embodiments may have a purity of about 99.50 wt % and a recovery of about 90.0 wt %, and in some embodiments, a purity of about 99.90 wt % or greater and a recovery of about 91.0 wt % or greater, and in some other embodiments, a purity of about 99.95 wt % or greater and a recovery of about 92.0 wt %. These purities of 1,4-diaminobutane are against other components excluding solvent, for example, water.

According to another aspect, there is provided a polyamide prepared using a 1,4-diaminobutane according to the above-described embodiments.

For example, polyamide 4,6 may be prepared by reacting 1,4-diaminobutane with adipic acid. For example, polyamide 4T may be prepared by reacting 1,4-diaminobutane with terephthalic acid. Various polyamides, not only polyamide 4,6 and polyamide 4T, may be prepared using a 1,4-diaminobutane according to the above-described embodiments.

MODE OF THE DISCLOSURE

One or more embodiments of the present disclosure will now be described in detail with reference to the following examples. However, these examples are only for illustrative purposes and are not intended to limit the scope of the one or more embodiments of the present disclosure.

(Purification of 1,4-diaminobutane)

EXAMPLE 1

1,4-diaminobutane Purification Method without Bacterial Cells Removal (Fermentation Step)

1 mL of a XQ37/pKKSpeC culture activated in a Luria-Bertani (LB) medium was added into a 350-mL baffled flask containing 50 mL of the same medium, and cultured at about 30° C. and about 220 rpm for about 24 hours to an optical density ($OD_{600}$) of about 5 to obtain a 1,4-diaminobutane-including fermentation solution. The stirring rate was automatically increased to about 850 rpm to keep dissolved oxygen (DO) content at 20% of saturated air. An additional feed solution added to maintain constant glucose concentration contained 500 g/L of glucose and 200 g/L of $(NH_4)_2SO_4$.

(First Concentration Step)

8,000 g of the 1,4-diaminobutane-including fermentation solution was put into a 10-L concentrator (available from Eyela) and then concentrated at a vapor temperature of about 47° C. and a pressure of about 80 mmHg to remove about 70% of a solvent from the 1,4-diaminobutane-including fermentation solution. The removed condensed water was about 5,600 g, and about 0.2 g of 1,4-diaminobutane was found to remain in the removed condensed water. Table 1 shows the results of component analysis before and after the first concentration step. The amounts of 1,4-diaminobutane, amino acid, organic acid, and ions were analyzed by high-performance liquid chromatography (HPCL), and the moisture contents were analyzed by the Karl-Fisher method.

TABLE 1

| Component | Fermentation solution (g) | Concentrate from first concentration (g) | Condensed water removed after first concentration (g) |
|---|---|---|---|
| water | 6760.8 | 1165.7 | 5595.1 |
| 1,4-diaminobutane | 288.6 | 288.4 | 0.2 |
| amino acid | 83.5 | 83.5 | 0.0 |
| ions | 463.1 | 458.4 | 4.6 |
| organic acid | 106.6 | 106.6 | 0.1 |
| bacterial cells | 297.4 | 297.4 | 0.0 |
| Total amount | 8000.0 | 2400.0 | 5600.0 |

(pH Adjustment Step)

1230 g of sodium hydroxide was added to 2400 g of the concentrate resulting from the first concentration to adjust pH to about 13.5.

(Recovery Step: Second Concentration Step)

The pH-adjusted concentrate (pH 13.5) was put into a 5L-double jacketed reactor in which top of the reactor was connected to the 10$^{th}$ tray (from a bottom) of a 30-trays distillation tower (available from Aceglass), and then further concentrated at a vapor temperature of about 50° C. to about 90° C. at a pressure of about 80 mmHg. The double jacketed reactor was maintained at a vapor temperature of about 47° C. at an initial stage due to water evaporation, and the vapor temperature was increased to about 90° C. with evaporation of 1,4-diaminobutane. The resulting vapor mainly including 1,4-diaminobutane was supplied into the 30-trays distillation tower.

(Recovery Step: Fractional Distillation Step)

The vapor mainly including 1,4-diaminobutane was supplied into the 30-trays distillation tower to recover 2042.6 g of water and ammonia in an upper region of the distillation tower, and 260.5 g of 1,4-diaminobutane in a lower region thereof (a purity of about 99.93 wt % (excluding water) as measured by HPLC) with a recovery of about 90.33 wt %.

The fractional distillation of 1,4-diaminobutane was performed in the distillation tower at a vapor temperature of about 50° C. to about 90° C. and at a pressure of about 80 mmHg.

Table 2 shows the results of component analysis in the pH adjustment and recovery steps. The amounts of 1,4-diaminobutane, amino acid, organic acid, and ions were analyzed by HPCL, and the moisture contents were analyzed by the Karl-fisher method.

EXAMPLE 2

Organic Amine Purification Method with Bacterial Cell Removal (Fermentation Step)

1 mL of a XQ37/pKKSpeC culture activated in a Luria-Bertani (LB) medium was added into a 350-mL baffled flask containing 50 mL of the same medium, and cultured at about 30° C. and about 220 rpm for about 24 hours to an $OD_{600}$ of about 5 to obtain a 1,4-diaminobutane-including fermentation solution. The stirring rate was automatically increased to about 850 rpm to keep dissolved oxygen (DO) content at 20% of saturated air. An additional feed solution added to maintain constant glucose concentration contained 500 g/L of glucose and 200 g/L of $(NH_4)_2SO_4$.

(Bacterial Cell Removal Step)

8,000 g of the 1,4-diaminobutane-including fermentation solution was put into a 15-L basket, and filtered through a cartridge type membrane filter (available from Milipore, Pellicon 2, pore size: 0.1 μm, membrane area: 0.5 m$^2$) at a temperature of about 50° C. and a transmembrane pressure (TMP) of about 1.2 atm to remove a bacterial cell sludge solution, thereby obtaining a filtrate.

(First Concentration Step)

The resulting filtrate from which bacterial cells were removed was about 7803.6 g, and the removed bacterial cell sludge solution was about 196.4 g. 7803.6 g of the filtrate from which bacterial cells were removed was put into a 10-L concentrator (available from Eyela) and then concentrated at a vapor temperature of about 47° C. and a pressure of about 80 mmHg to remove about 70% of water from the 1,4-diaminobutane-including fermentation solution. The removed condensed water was about 5,462.5 g, and about 0.3 g of 1,4-diaminobutane was found to remain in the removed condensed water. Table 3 shows the results of component analysis before and after the bacterial cell removal step and the first concentration step. The amounts of 1,4-diaminobutane, amino acid, organic acid, and ions were analyzed by HPCL, and the moisture contents were analyzed by the Karl-fisher method.

TABLE 2

| Component | pH-adjusted concentrate after first concentration (g) | Concentrate recovered in lower region of distillation tower (g) | Concentrate recovered in upper region of distillation tower (g) | Residue from second concentration (g) |
|---|---|---|---|---|
| water | 2042.1 | 3.9 | 1975.2 | 63.0 |
| 1,4-diaminobutane | 288.4 | 260.5 | 9.2 | 18.7 |
| amino acid | 83.5 | 0.0 | 0.0 | 83.5 |
| ions | 812.1 | 0.1 | 58.2 | 753.8 |
| organic acid | 106.6 | 0.0 | 0.0 | 106.5 |
| bacterial cells | 297.4 | 0.0 | 0.0 | 297.4 |
| Total amount | 3630.0 | 264.5 | 2042.6 | 1322.9 |

TABLE 3

| Component | Fermentation solution (g) | Bacterial cell sludge solution (g) | Filtrate from which bacterial cells were removed (g) | Concentrate after first condensation (g) | Condensed water removed after first condensation (g) |
| --- | --- | --- | --- | --- | --- |
| water | 6760.8 | 140.4 | 6880.6 | 1422.8 | 5457.8 |
| 1,4-diaminobutane | 288.6 | 5.8 | 282.9 | 282.6 | 0.3 |
| amino acid | 83.5 | 1.7 | 81.8 | 81.8 | 0.0 |
| ions | 463.1 | 9.3 | 453.8 | 449.4 | 4.4 |
| organic acid | 106.6 | 2.1 | 104.5 | 104.4 | 0.1 |
| bacterial cells | 297.4 | 37.2 | 0.0 | 0.0 | 0.0 |
| Total amount | 8000.0 | 196.4 | 7803.6 | 2341.1 | 5462.5 |

(pH Adjustment Step)

1205.4 g of sodium hydroxide was added to 2341.1 g of the concentrate resulting from the first concentration to adjust pH to about 13.5.

(Recovery Step: Second Concentration Step)

The pH-adjusted concentrate (pH 13.5) was put into a 5L-double jacketed reactor in which top of the reactor was connected to the $10^{th}$ tray (from a bottom) of a 30-trays distillation tower (available from Aceglass), and then further concentrated at a vapor temperature of about 50° C. to about 90° C. at a pressure of about 80 mmHg. The double jacketed reactor was maintained at a vapor temperature of about 47° C. at an initial stage due to water evaporation, and the vapor temperature was increased to about 90° C. with evaporation of 1,4-diaminobutane. The resulting vapor mainly including 1,4-diaminobutane was supplied into the 30-trays distillation tower.

(Recovery Step: Fractional Distillation Step)

The vapor mainly including 1,4-diaminobutane was supplied into the 30-trays distillation tower to recover 2279.0 g of water and ammonia in an upper region of the distillation tower, and 268.5 g of 1,4-diaminobutane in a lower region thereof (a purity of about 99.97 wt % (excluding water) as measured by HPLC) with a recovery of about 95.01 wt %.

The fractional distillation of 1,4-diaminobutane was performed in the distillation tower at a vapor temperature of about 50° C. to about 90° C. and at a pressure of about 80 mmHg.

Table 4 shows the results of component analysis at the pH adjustment and recovery steps. The amounts of 1,4-diaminobutane, amino acid, organic acid, and ions were analyzed by HPCL, and the moisture contents were analyzed by the Karl-fisher method.

EXAMPLE 3

1,4-diaminobutane was purified in the same manner as in Example 2, except that the pH of the concentrate from the first concentration step was adjusted to about 12.3. The recovery of 1,4-diaminobutane recovered in a lower region of the distillation tower was about 67.6 wt %.

EXAMPLE 4

1,4-diaminobutane was purified in the same manner as in Example 2, except that the pH of the concentrate from the first concentration step was adjusted to about 12.5. The recovery of 1,4-diaminobutane recovered in a lower region of the distillation tower was about 75.8 wt %.

COMPARATIVE EXAMPLE 1

1,4-diaminobutane was purified in the same manner as in Example 2, except that the pH of the concentrate from the first concentration step was adjusted to about 11.8. The recovery of 1,4-diaminobutane recovered in a lower region of the distillation tower was about 6.9 wt %.

EVALUATION EXAMPLE 1

The recovery of 1,4-diaminobutane obtained in Examples 2 to 4 and Comparative Example 1 are shown in Table 5, together with the pHs of the concentrates from the first concentration after the pH adjustment in Examples 2 and 4 and Comparative Example 1, to evaluate a variation in recovery of 1,4-diaminobutane depending on the pH of the concentrate after the first concentration.

TABLE 4

| Component | pH-adjusted concentrate (g) | Concentrate recovered in lower region of distillation tower (g) | Concentrate recovered in upper region of distillation tower (g) | Residue from second concentration (g) |
| --- | --- | --- | --- | --- |
| water | 2281.7 | 3.2 | 2213.3 | 65.1 |
| 1,4-diaminobutane | 282.6 | 268.5 | 8.5 | 5.7 |
| amino acid | 81.8 | 0.0 | 0.0 | 81.8 |
| ions | 796.0 | 0.0 | 57.1 | 738.8 |
| organic acid | 104.4 | 0.0 | 0.0 | 104.4 |
| bacterial cells | 0.0 | 0.0 | 0.0 | 0.0 |
| Total amount | 3546.5 | 271.7 | 2279.0 | 995.8 |

TABLE 5

| Example | pH of basic composition | Recovery of 1,4-diaminobutane [wt %] |
|---|---|---|
| Comparative Example 1 | 11.8 | 6.9 |
| Example 3 | 12.3 | 67.6 |
| Example 4 | 12.5 | 75.8 |
| Example 2 | 13.5 | 95.0 |

Referring to Table 5, the concentrates from the first concentration after pH adjustment in Examples 2 to 4 had a basic pH of about 12 or greater, and consequently Examples 2 to 4 showed a markedly enhanced recovery of 1,4-diaminobutane.

INDUSTRIAL APPLICABILITY

As described above, high-purity 1,4-diaminobutane may be obtained with a high yield by adding a base to a 1,4-diaminobutane-including fermentation solution.

The invention claimed is:

1. A method of purifying 1,4-diaminobutane, the method comprising:
    concentrating a fermentation solution comprising at least one of 1,4-diaminobutane and a salt thereof to obtain a concentrate;
    adding a base to the concentrate of the fermentation solution to prepare an basic composition having a pH higher than 12; and
    recovering 1,4-diaminobutane from the basic composition.

2. The method of claim 1, wherein at least part of a solvent in
    the fermentation solution is removed during the concentrating of the fermentation solution.

3. The method of claim 1, wherein the concentrating of the fermentation solution is performed at a vapor temperature of about 100° C. or less.

4. The method of claim 1, wherein the concentrating of the fermentation solution is performed at a pressure of 760 mmHg or less.

5. The method of claim 1, wherein the concentrating of the fermentation solution is performed at a vapor temperature of about 10° C. to about 100° C. and a pressure of about 10 mmHg to about 760 mmHg.

6. The method of claim 1, further comprising removing bacterial cells from the fermentation solution before the concentrating of the fermentation solution.

7. The method of claim 1, wherein the amount of the solvent in the concentrate is in a range of about 10 wt % to about 50 wt % based on a total weight of the concentrate.

8. The method of claim 1, wherein the base is at least one selected from the group consisting of sodium hydroxide, calcium hydroxide, magnesium hydroxide, potassium hydroxide, barium hydroxide, and ammonium hydroxide.

9. The method of claim 1, wherein the basic composition has a pH higher than 12.0 to about 14.0.

10. The method of claim 1, wherein the recovering of 1,4-diaminobutane from the basic composition comprises:
    separating an 1,4-diaminobutane—including composition from the basic composition by distillation; and
    recovering 1,4-diaminobutane from the 1,4-diaminobutane—including composition by fractional distillation.

11. The method of claim 10, wherein the separating of the 1,4-diaminobutane—including composition is performed at a vapor temperature of about 30° C. to about 158° C. at a pressure of about 10 mmHg to about 760 mmHg.

12. The method of claim 10, wherein the 1,4-diaminobutane—including composition is in a gaseous state, a liquid state, or a mixed state thereof.

13. The method of claim 10, wherein the separating of the 1,4-diaminobutane—including composition from the basic composition by distillation and the recovering of 1,4-diaminobutane from the 1,4-diaminobutane—including composition by fractional distillation are continuously performed.

14. The method of claim 10, wherein the recovering of 1,4-diaminobutane by fractional distillation is performed using a distillation tower.

15. The method of claim 14, wherein the distillation tower is operated at a vapor pressure of about 30° C. to about 158° C. and a pressure of about 10 mmHg to about 760 mmHg.

16. The method of claim 14, wherein 1,4-diaminobutane is recovered in a lower region of the distillation tower.

17. The method of claim 10, further comprising recovering a byproduct from the basic composition after the separating of the 1,4-diaminobutane—including composition.

18. The method of claim 17, wherein the byproduct is at least one selected from the group consisting of sodium sulfate, potassium sulfate, calcium sulfate, magnesium sulfate, lithium sulfate, barium sulfate, and ammonium sulfate.

19. 1,4-diaminobutane purified by the method of claim 1.

20. A polyamide prepared using the 1,4-diaminobutane of claim 19.

* * * * *